United States Patent [19]

Grimard

[11] Patent Number: 5,795,337
[45] Date of Patent: Aug. 18, 1998

[54] SYRINGE ASSEMBLY AND SYRINGE STOPPER

[75] Inventor: Jean Pierre Grimard, Vif, France

[73] Assignee: Becton Dickinson and Company, Franklin Lakes, N.J.

[21] Appl. No.: 630,338

[22] Filed: Apr. 10, 1996

Related U.S. Application Data

[63] Continuation of Ser. No. 196,349, Feb. 14, 1994, abandoned.

[51] Int. Cl.$^6$ ............................................. A61M 5/315
[52] U.S. Cl. ........................................ 604/222; 604/228
[58] Field of Search ............................ 604/218, 219, 604/222, 228, 230, 82, 90, 110, 191, 195

[56] References Cited

U.S. PATENT DOCUMENTS

| | | | |
|---|---|---|---|
| 511,600 | 12/1893 | Ellis | 215/355 |
| 729,835 | 6/1903 | Barnes et al. | 215/355 X |
| 782,723 | 2/1905 | Campbell | 604/218 |
| 3,331,538 | 7/1967 | Higgins | 604/222 X |
| 3,901,402 | 8/1975 | Ayres | 604/281 X |
| 3,967,759 | 7/1976 | Baldwin et al. | 604/218 X |
| 4,030,496 | 6/1977 | Stait et al. | 604/222 |
| 4,215,701 | 8/1980 | Raitto | 128/763 |
| 4,492,576 | 1/1985 | Dragan | 433/90 |
| 4,500,310 | 2/1985 | Christinger | 604/228 |
| 4,599,082 | 7/1986 | Grimard | 604/90 |
| 4,610,669 | 9/1986 | Meyer et al. | 604/218 |
| 4,932,941 | 6/1990 | Min et al. | 604/110 |
| 5,007,904 | 4/1991 | Densmore et al. | 604/228 |
| 5,254,093 | 10/1993 | Bartlett et al. | 604/110 |
| 5,314,416 | 5/1994 | Lewis et al. | 604/219 |
| 5,458,576 | 10/1995 | Haber et al. | 604/222 |

*Primary Examiner*—Wynn Wood Coggins
*Assistant Examiner*—A. T. Nguyen
*Attorney, Agent, or Firm*—Allen W. Wark

[57] ABSTRACT

A syringe stopper for use in a syringe barrel having a substantially cylindrical body comprises a piston-like stopper body for slidable fluid-tight engagement inside the barrel of the syringe. The body includes a distal end, a proximal end and a longitudinal axis therethrough. A distally directed, conically-shaped projection is positioned on the distal end of the stopper body. At least one elongate discontinuity, running along the conically-shaped projection, is provided. The discontinuity includes a first end on the conically-shaped projection and extends radially outwardly therefrom to a second end, as viewed from the distal end of the stopper. The discontinuity may be in the form of a raised rib or a recessed groove.

21 Claims, 7 Drawing Sheets

SYRINGE ASSEMBLY AND SYRINGE STOPPER

This application is a continuation of application Ser. No. 08/196,349, filed Feb. 14, 1994, now abandoned.

FIELD OF THE INVENTION

The present invention relates to syringes and syringe stoppers and more particularly concerns a syringe stopper which helps provide for a more complete expulsion of the contents of the syringe at the time of drug delivery.

DESCRIPTION OF THE PRIOR ART

Prior art hypodermic syringes include an elongate barrel having opposed proximal and distal ends and a chamber therebetween for receiving a fluid. A passageway extends through the distal end of the syringe barrel and communicates with the chamber. The distal end of the syringe barrel is connected to a needle cannula for delivering fluid from the chamber and passageway. The proximal end of the syringe barrel slidably receives a plunger rod and stopper assembly, such that force applied to the plunger rod urges the stopper along the barrel to drive liquid from the chamber through the needle cannula.

A problem with some prior art hypodermic syringes involves the amount of liquid which can remain in the barrel after the stopper is advanced the full length of the barrel during the injection process. There remains in every syringe a certain residual volume, no matter how small, which is trapped between the end of the stopper and the needle tip, including the volume of the needle cannula and the volume of the extreme distal end of the syringe barrel. For very expensive liquid medications and medications which require very precise dose delivery it may be necessary to overfill the barrel for the amount of the dead space so that the dose delivered will be the dose desired and the additional medication will be disposed of with the used syringe. Over many of syringes the amount of unused medication can become substantial.

One way to minimize dead space is to carefully control the dimensions of the inside of the syringe barrel and to conform the distal end of the stopper as closely as possible to the syringe barrel dimensions. This solution is not a complete answer because, especially in the case of glass syringe barrels, the interior shape of the barrel, as it transitions between the bore of the chamber to the needle holding tip cannot be as precisely controlled as an injection molded plastic barrel. Further, when the angle of the stopper tip is designed to conform with the interior angle of the barrel, variations in dimensions experienced in the manufacturing process can result in angular variations between the surfaces of the stopper and the barrel interior wherein the distal portion of the stopper is capable of occluding the passageway at the distal end of the barrel and trapping fluid in the barrel behind the distal end of the stopper.

Accordingly, there is still a need for syringe stoppers which help minimize dead space and help assure that liquid medication is not trapped in the barrel when the stopper occludes or blocks off the exit passageway in the barrel.

SUMMARY OF THE INVENTION

The syringe stopper of the present invention, for use in a syringe barrel having a substantially cylindrical body, comprises a piston-like stopper body for slidable fluid-tight engagement inside the barrel of the syringe. The body includes a distal end, a proximal end and a longitudinal axis therethrough. A distally directed, conically-shaped projection is provided on the distal end of the stopper body. At least one elongate discontinuity, running along the conically-shaped projection, is provided. The at least one elongate discontinuity has a first end on the conically-shaped projection and extends radially outwardly therefrom to a second end, as viewed from the distal end of the stopper. The at least one elongate discontinuity can be in the form of a raised rib or a recessed groove and may include a plurality of discontinuities.

The stopper can be combined with a syringe barrel having an open proximal end, a distal end and a cylindrical body portion therebetween which defines a chamber for retaining liquid. The stopper, in the combination, is positioned in fluid-tight engagement inside the barrel so the distal end of the stopper faces the distal end of the barrel. The distal end of the barrel includes an aperture therethrough in fluid communication with the chamber. In some applications, the proximal end of the stopper may be connected to the distal end of a rigid elongate plunger rod.

DETAILED DESCRIPTION

Figure 1:
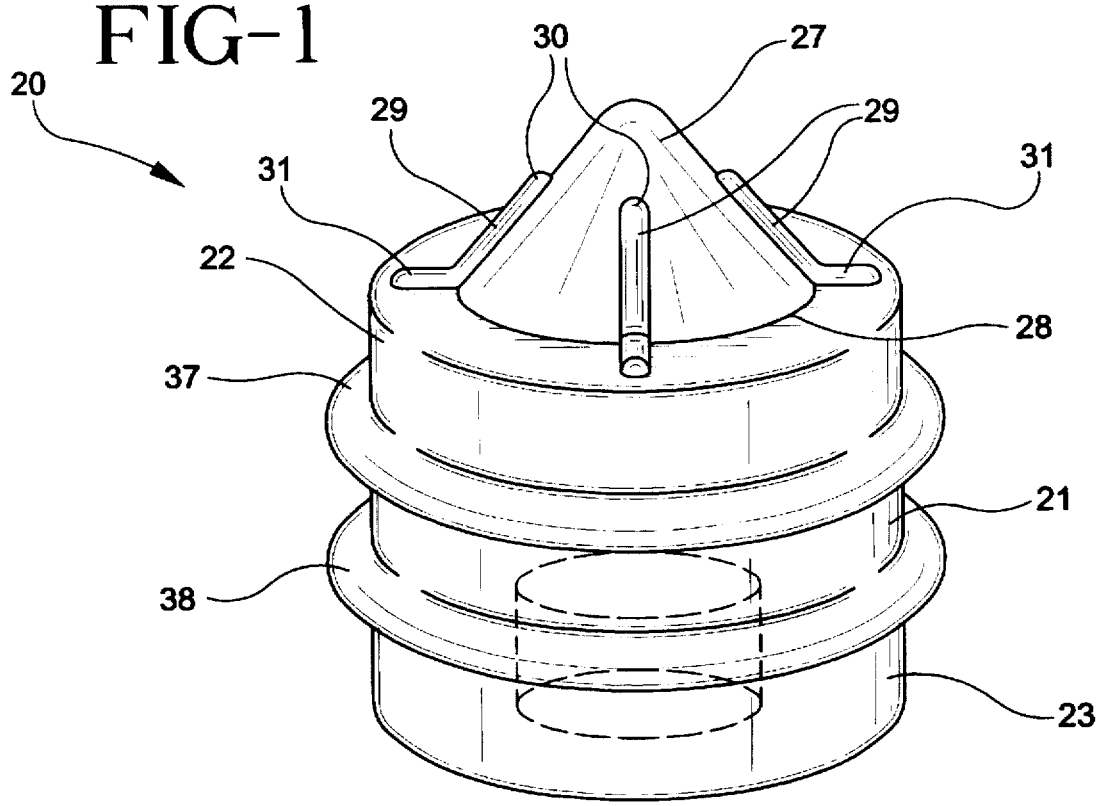
FIG. 1 is a perspective view of a hypodermic syringe stopper in accordance with the present invention.
Figure 2:
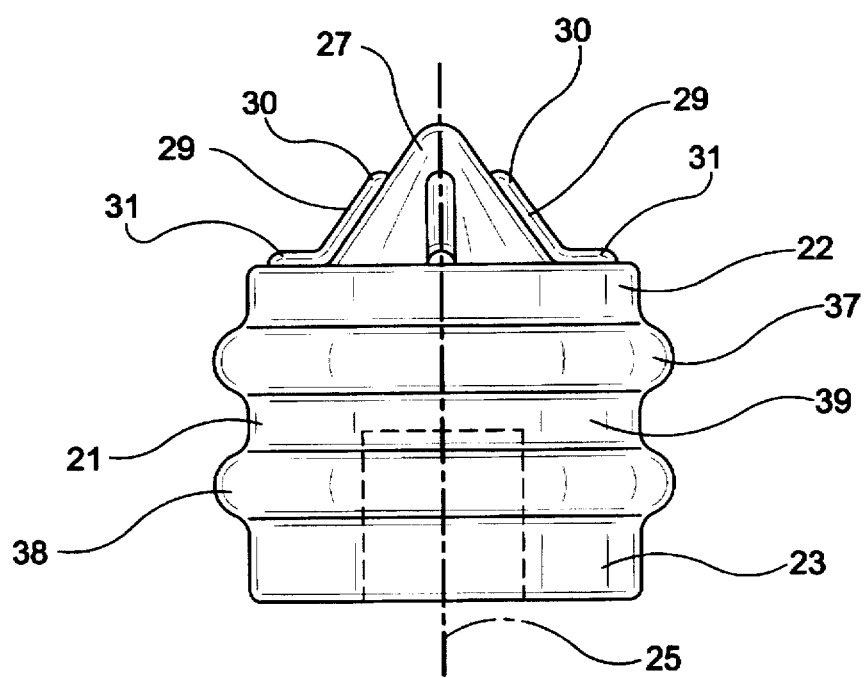
FIG. 2 is a side elevational view of the stopper of FIG. 1.

While this invention is satisfied by embodiments in many different forms, there are shown in the drawings and will be herein described in detail preferred embodiments of the invention with the understanding that the present disclosure is to be considered exemplary of the principles of the invention and is not intended to limit the scope of the invention to the embodiments illustrated. The scope of the invention will be measured by the appended claims and their equivalents.

Adverting to FIGS. 1–4 syringe stopper 20 is intended for use in a syringe barrel having a substantially cylindrical body. Stopper 20 includes a piston-like stopper body 21 for slidable fluid-tight engagement inside the barrel of the syringe. The stopper body includes a distal end 22, a proximal end 23 and a longitudinal axis 25 therethrough. Stopper body 21 also includes annular rib 37 at distal end 22 and annular rib 38 located proximally from rib 37. Recess 39 is located between ribs 37 and 38 and has a diameter which is less than the diameter of the ribs. The ribs are intended to provide a stable fluid-tight seal between the stopper body and the syringe barrel.

For the purposes of the description of the present invention, the term "distal end" is intended to refer to the end of the syringe from which the needle projects and the end of the stopper which is closer to the syringe needle, whereas the term "proximal end" is intended to refer to the end of the syringe closer to the holder of the syringe and furthest from the needle tip and the end of the stopper furthest from the needle tip.

Figure 3:
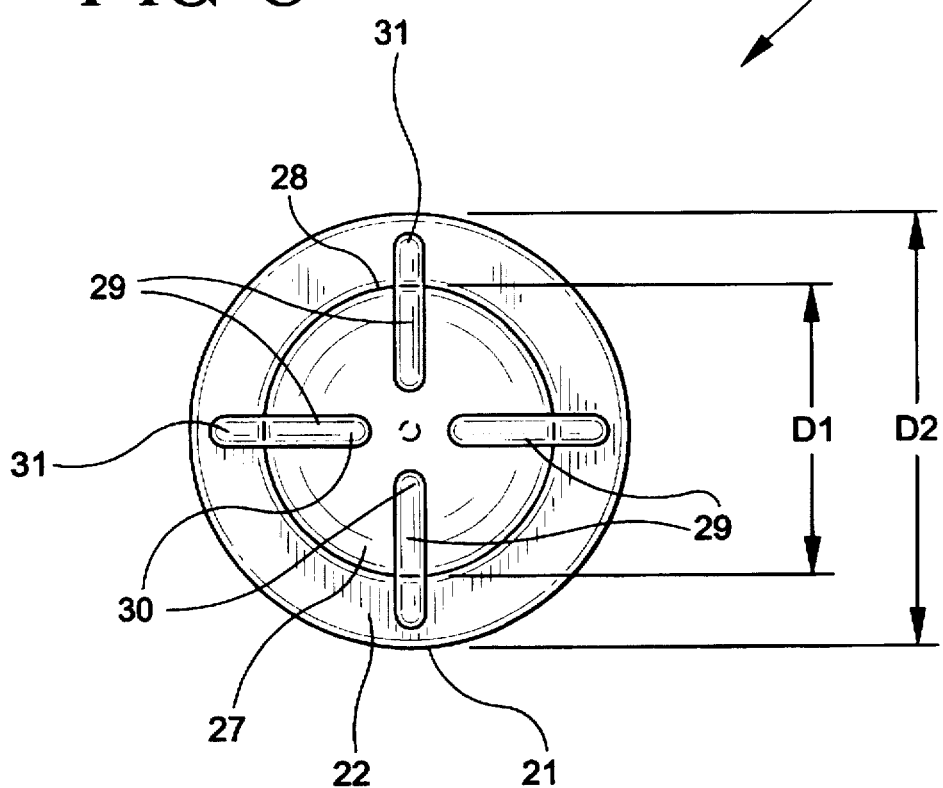
FIG. 3 is a top plan view of the stopper of FIG. 2.
Figure 4:
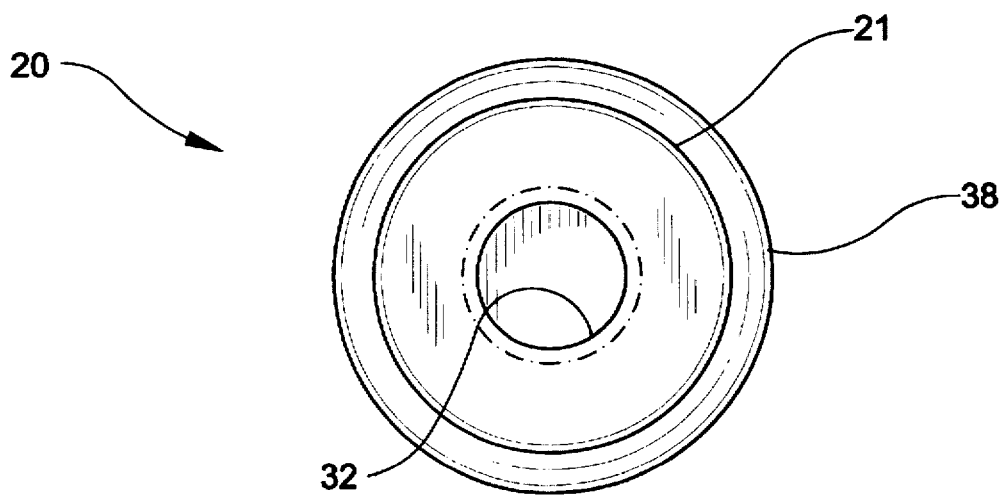
FIG. 4 is a bottom plan view of the stopper of FIG. 2.
Figure 8:
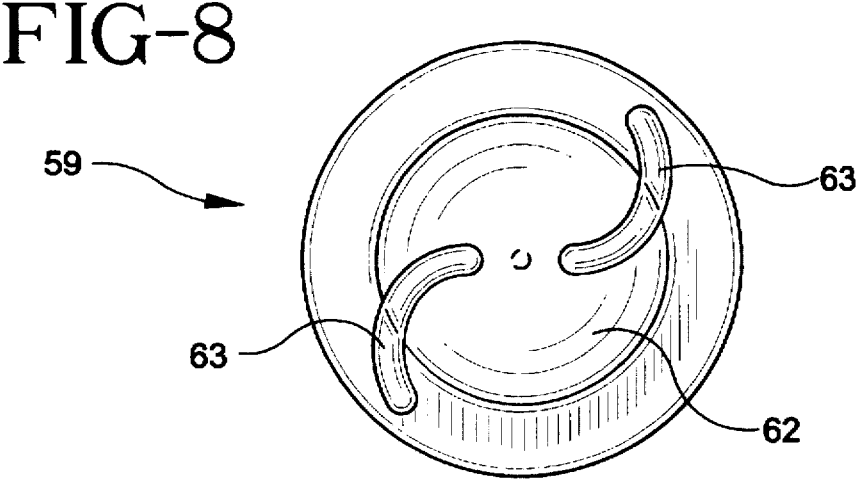
FIG. 8 is a top plan view of another alternate embodiment of the stopper of the present invention.
Figure 9:
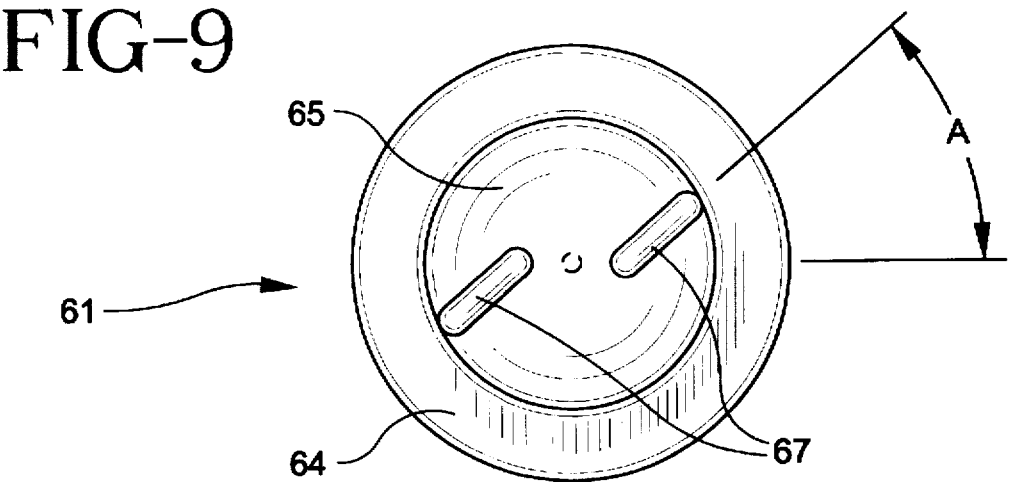
FIG. 9 is a top plan view of still another alternate embodiment of the stopper of the present invention.

A distally directed conically-shaped projection 27 is located on the distal end of the stopper body. In this embodiment, the conically-shaped projection intersects the distal end of the stopper at intersection 28 which defines diameter D1 as best illustrated in FIG. 3. This intersection results in the diameter D1 being smaller than diameter D2 of the stopper body. This is the preferred configuration of the stopper of the present invention. At least one elongate discontinuity is provided. The elongate discontinuity runs along the conically-shaped projection 27. In this embodiment, there are a plurality of discontinuities which are in the shape of raised ribs 29. For the purposes of the present invention, the discontinuities may be confined to the surface of the conically shaped projection. However, it is preferred that the discontinuities also continue past the base of the conical projection and onto the distal end of the stopper body. In this embodiment, raised ribs 29 run along projection 27 from a first end 30 to a second end 31 on the distal end of the stopper. The projections extend radially outwardly from first end 30 to second end 31 as best illustrated in FIG. 3. It is not necessary that the discontinuities extend in a straight radial direction as illustrated in FIG. 3 but also can extend in a generally radial direction such as illustrated in FIGS. 8 and 9 and which will be discussed in more detail hereinafter. Also, as previously indicated, the second end of the projection can terminate at intersection 28 between the conical projection and the distal end of the stopper body.

Figure 5:
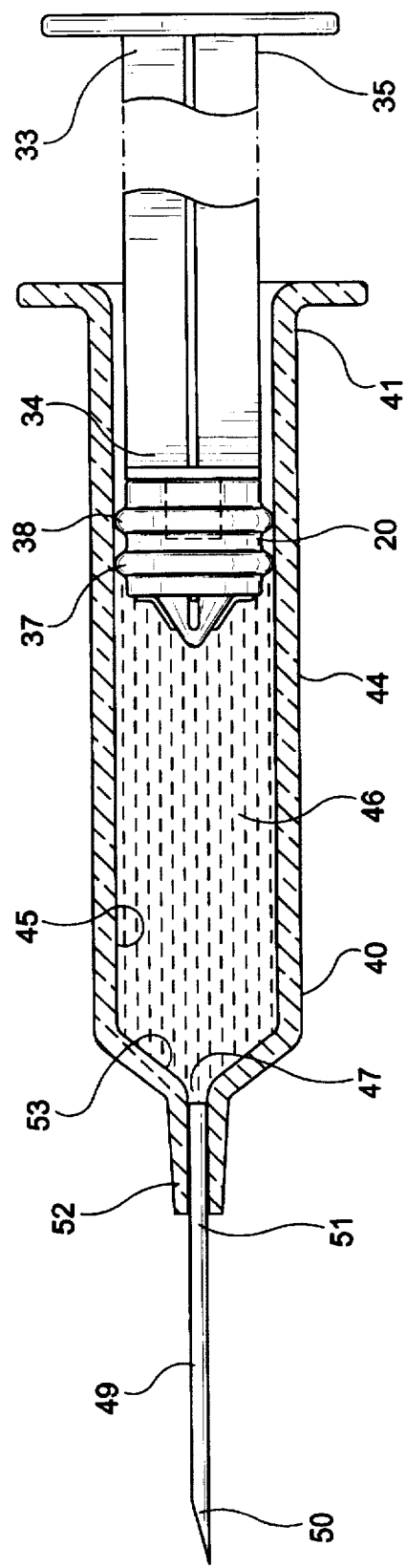
FIG. 5 is a side elevational partial cross-sectional view of a syringe assembly utilizing the stopper of FIG. 1.
Figure 6:
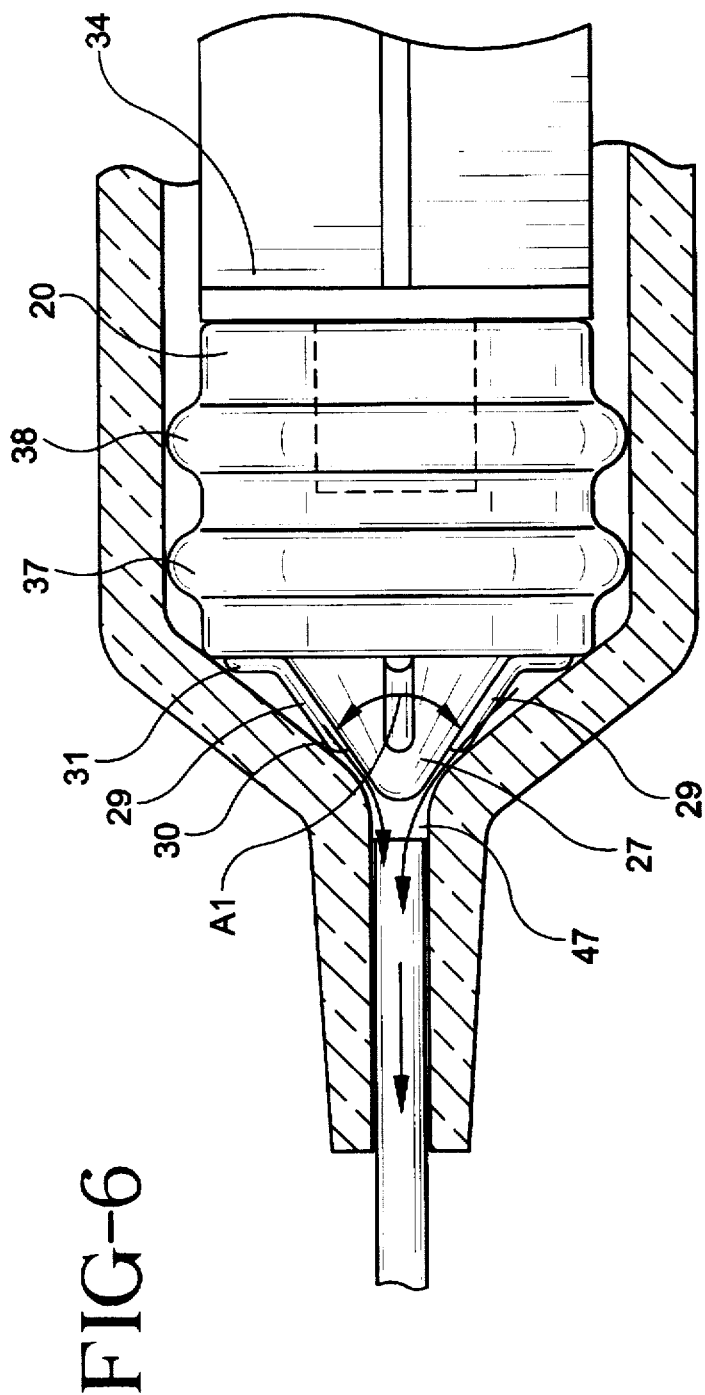
FIG. 6 is an enlarged partial cross-sectional view of the syringe of FIG. 5 showing the stopper in a fully advanced position expelling the last portion of the medication.

Referring now to FIGS. 1–6 together, the stopper of FIGS. 1–4 is illustrated in a syringe assembly of FIGS. 5 and 6. The stopper of the present invention is intended to be the last stopper in any syringe assembly. As will be described in more detail hereinafter, some syringe assemblies have several stoppers and the unique features of the stopper of the present invention are intended for the stopper which contacts the end of the syringe barrel. In some syringe devices this may be a floating stopper which is not connected to a plunger rod. For the purposes of discussion, a one-stopper syringe is illustrated in FIGS. 5 and 6. The syringe assembly includes plunger rod 33 having a distal end 34 and a proximal end 35. Distal end 34 of the plunger rod is connected to stopper body 21 through the action of a threaded tip on the distal end of the plunger rod (not shown) which engages a threaded recess 32 in the stopper body. It should be noted that there are many ways to join a plunger rod to the stopper and that the threaded engagement is exemplary of many possibilities. For example, the stopper may include a cavity in the proximal end of the stopper body which has a reduced diameter or neck at the proximal end of the cavity. This cavity could be shaped to accept a tip on the distal end of the plunger rod which has an enlarged distal end so that the parts will come together in a snap-fit arrangement. The stopper may be adhesively attached to the plunger rod. The plunger rod and the stopper could be integrally molded through a two-shot molding process wherein a soft thermoplastic elastomer is injected on the distal or stopper end of the mold cavity and a more rigid plastic is injected on the proximal end of the mold cavity.

Syringe barrel 40 includes open proximal end 41, distal end 43 and a cylindrical body portion 44 therebetween defining chamber 45 for retaining liquid such as liquid medication 46. The syringe barrel of this embodiment is made of glass or at least partially of glass, such as a glass barrel having a plastic flange at its proximal end. As best illustrated in FIGS. 5 and 6, stopper 20 is positioned in fluid-tight engagement inside the barrel through the action of annular ribs 37 and 38 with the distal end of the stopper facing the distal end of the syringe barrel. Distal end 43 of the syringe barrel includes a passageway 47 which is in fluid communication with chamber 45. Elongate needle cannula 49 includes distal end 50, a proximal end 51 and a lumen therethrough. Proximal end 51 of the needle cannula is connected to distal end 43 of the barrel so that the lumen is in fluid communication with chamber 45 through passageway 47. In this embodiment the needle cannula is permanently attached to the syringe barrel through the use of adhesives. It is within the purview of the present invention to include needles which are removably attached to the syringe barrel such as through a needle hub which is permanently attached to the needle cannula and frictionally attached to tip 52 at the distal end of the syringe barrel.

It is more difficult to control the shape of the interior of the syringe barrel at the distal end in the area identified by numeral 53 which is between tip 52 and cylindrical body portion 44 of the barrel. The stopper of the present invention is capable of helping to expel liquid 46 from the barrel while minimizing the potential for liquid being trapped in the barrel by the stopper. This result can be accomplished even though the shape of the barrel interior in area 53 may not be precisely held from syringe barrel to syringe barrel, such as in a glass barrel process. Referring to FIG. 6, a conically-shaped projection such as projection 27 may, without the discontinuities, have a tendency to block the passageway of the barrel before all of the liquid 46 escapes from the barrel. Discontinuities, such as raised ribs 29, act to prevent the immediate sealing of passageway 47 by the stopper. Accordingly, trapped liquid 46 can run along raised ribs 29 and through the passageway and into the needle cannula lumen. Since the stopper 21 is made of resilient material, further pressure on the plunger rod in a distal direction will distort the stopper squeezing liquid through the passageway which is being temporarily held open by ribs 29.

The inventor has found that good results are achieved by sizing the conically-shaped projection so that diameter D1, of the projection base, is preferably forty to sixty percent as large as stopper body diameter D2 and desirably thirty to eighty percent of the stopper diameter D2. Experiments were run with a glass syringe barrel with stoppers having diameters ranging from 8.65 mm to 14.25 mm and a conically-shaped projection having a total included angle of 80° which is illustrated as A1 in FIG. 6. To obtain a resilient stopper it is preferred that the stopper be made of natural rubber, synthetic rubber, thermoplastic elastomers or combinations thereof.

Figure 7:
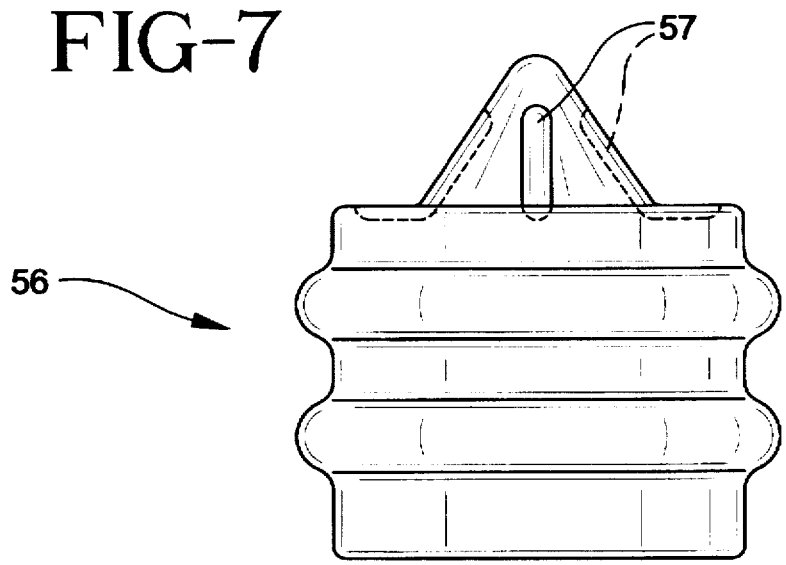
FIG. 7 is a side elevational view of an alternate embodiment of the stopper of the present invention.

Referring to FIG. 7, an alternative stopper 56 is illustrated. Stopper 56 is substantially the same in shape and function to the stopper of FIGS. 1–4 with the exception that the discontinuities in stopper 56 comprise recessed grooves 57 which perform the same function as the raised ribs 29 of stopper 20 previously described. Accordingly stopper 56 performs in the same manner as described hereinabove with trapped liquid escaping through recess grooves 57.

Referring to FIGS. 8 and 9 alternative stoppers 59 and 61 are illustrated. FIGS. 8 and 9 are top plan views of the stoppers showing the distal end of each stopper. Stopper 59 includes conically-shaped projection 62 and discontinuities in the form of curvilinearly-shaped raised ribs 63. Stopper 61 includes conically-shaped projection 65 and discontinuities in the form of raised ribs 67. Raised ribs 67 are straight ribs as in the embodiment of FIGS. 1–4. Ribs 67 are slightly angled to the radius so that they extend radially outwardly but at an angle to the true radius. Also raised ribs 67 begin and end on the surface of conically shaped projection 65 and do not extend onto distal end 64 of the stopper.

Figure 10:
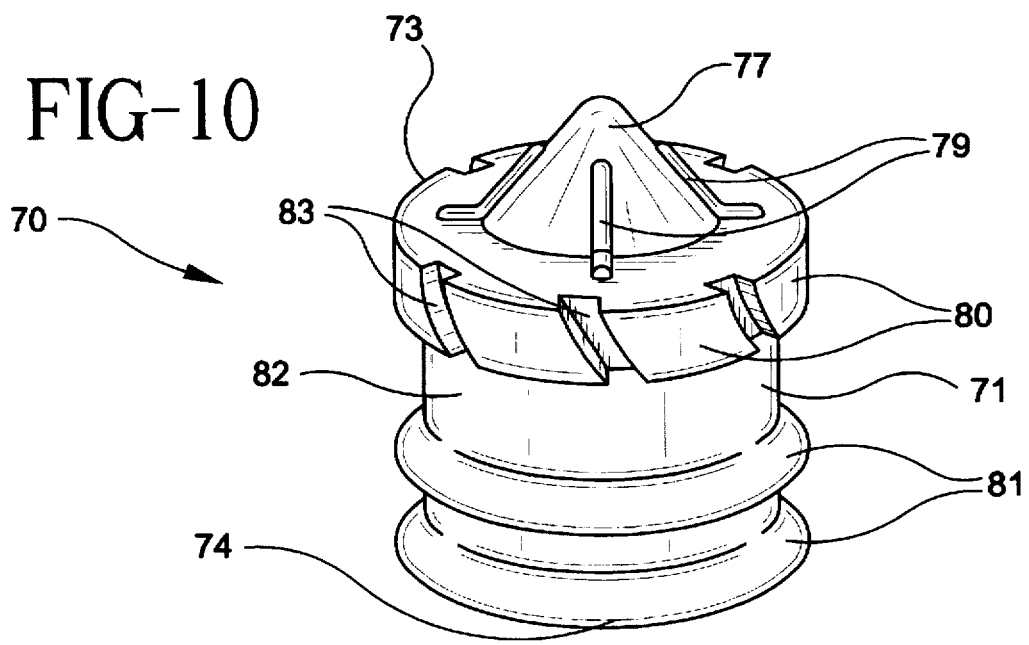
FIG. 10 is a perspective view of another stopper configuration of the present invention.
Figure 11:
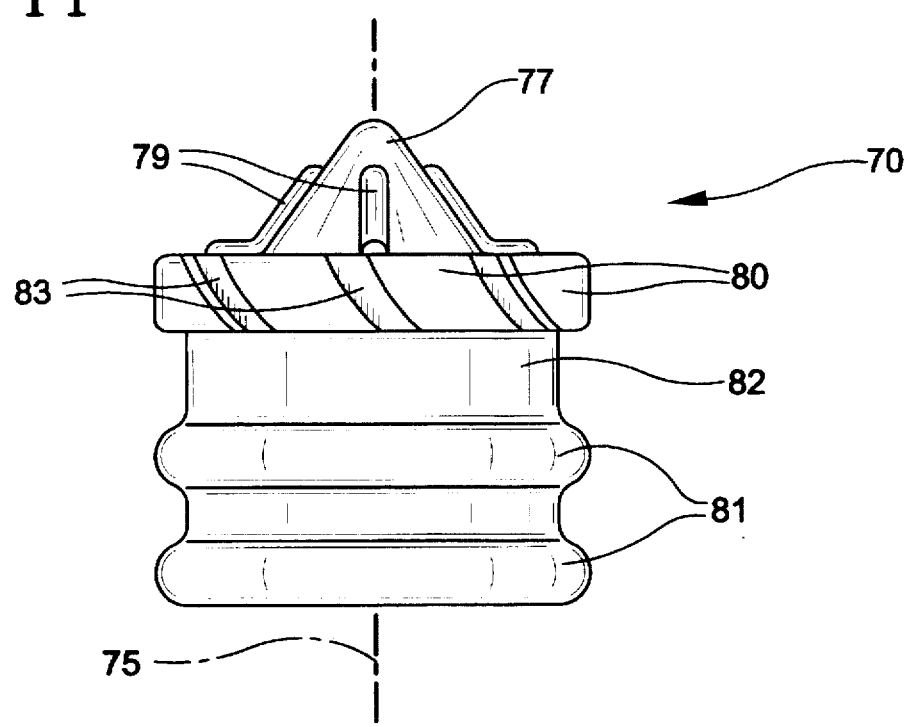
FIG. 11 is a side-elevational view of the stopper of FIG. 10.
Figure 12:
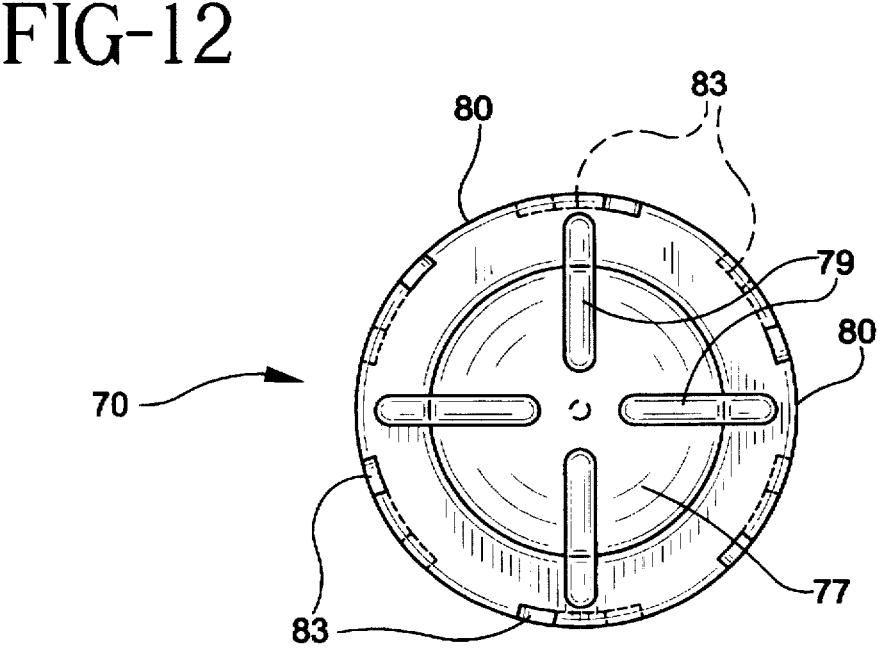
FIG. 12 is a top plan view of the stopper of FIG. 11.

Referring to FIGS. 10–12, an alternative stopper 70 is illustrated. Stopper 70 is similar to the stopper taught in U.S. Pat. No. 4,599,082, and can also be used in a two-component mixing syringe as taught in U.S. Pat. No. 4,599,082.

Stopper 70 includes a piston-like stopper body 71 having a distal end 73 and a proximal end 74. Conically-shaped projection 77 projects distally outwardly from distal end 73 of the stopper body. The conically-shaped projection further includes discontinuities in the form of raised ribs 79. This embodiment is illustrated with four ribs for ease of viewing. The invention requires at least one discontinuity and three discontinuities in the form of raised ribs are preferred. Stopper 70 includes annular rib 80 at distal end 73 and one or more annular ribs 81 near proximal end 74. Annular recess 82 is positioned between ribs 80 and 81. Annular recess 82 has a diameter less than the diameter of the ribs. Rib 80 further includes at least one groove 83 for allowing fluid communication therethrough. The function of the groove is taught in U.S. Pat. No. 4,599,082 and such teaching is incorporated herein by reference. The groove is used to promote the mixing of a wet and dry component in a by-pass syringe having a substantially cylindrical barrel with a by-pass zone which allows fluid to pass around ribs 81, when said ribs are in the by-pass zone through the recess and through grooves 83. Multiple grooves are preferred and grooves placed at an angle of 30° to 80° from longitudinal axis 75 of the stopper body are preferred. The stopper will function as a mixing stopper in a two-component syringe and will also function as the other stoppers described in FIGS. 1–9 to help prevent liquid from being trapped in the syringe barrel. It should also be noted that stopper 70 can be used in a lyophilizing process wherein the stopper is inserted in a liquid filled syringe barrel so that rib 80 engages the syringe barrel at its open proximal end and ribs 81 are outside of the barrel. The lyophilization process may then proceed with vapors escaping through grooves 83. At the end of the process, the syringe, while being subject to a subatmospheric environment, is sealed by pushing the stopper in a distal direction so that ribs 81 engage the inside of the syringe barrel.

All of the stoppers taught herein have unique structure which helps prevent liquid from being trapped in the syringe barrel at the end of the injection stroke and, accordingly, are improvements over the prior art.

I claim:

1. A syringe stopper made of a resilient material for use in a syringe barrel having a substantially cylindrical body comprising:

a piston-like stopper body for slidable fluid-tight engagement inside the barrel of the syringe, said stopper body having an outside diameter, a distal end, a proximal end and a longitudinal axis therethrough;

a conically-shaped projection on said distal end of said stopper body and projecting outwardly therefrom, said conically-shaped projection defining a base as it intersects said distal end of stopper body, said base having a base diameter less than said outside diameter of said stopper body to provide an exposed portion of said stopper body between the base of the conically-shaped projection and the distal end the stopper body; and a plurality of elongated discontinuities running along said conically-shaped projection in the form of raised ribs and continuing past the base of the conically-shaped projection into the exposed portion along the distal end of the stopper body, said raised ribs each having a first end on said conically-shaped projection and extending radially outwardly from the longitudinal axis of the stopper body to a second end disposed past the intersection of said base diameter and said distal end of the stopper body on said exposed portion of the distal end of said stopper body.

2. The syringe stopper of claim 1 in combination with a syringe barrel, said barrel having an open proximal end, a distal end and a cylindrical body portion therebetween defining a chamber for retaining liquid, said stopper body positioned in fluid-tight engagement inside said barrel so that said distal end of said stopper faces said distal end of said barrel, said distal end of said barrel having an aperture therethrough in fluid communication with said chamber.

3. The combination of claim 2 wherein said syringe barrel is made at least partially of glass.

4. The combination of claim 2 further including an elongate needle cannula having a distal end, a proximal end and a lumen therethrough, said proximal end of said needle cannula being connected to said distal end of said barrel so that said lumen is in fluid communication with said chamber.

5. The combination of claim 4 wherein said needle cannula is irremovably connected to said barrel.

6. The syringe stopper of claim 1 wherein said stopper body includes at least two annular ribs and a recess therebetween, said ribs having an outside diameter greater than the diameter of said recess.

7. The syringe stopper of claim 1 wherein said raised ribs are substantially straight when viewed from said distal end of said stopper body.

8. The syringe stopper of claim 1 wherein said raised ribs are curvilinearly shaped when viewed from said distal end of said stopper body.

9. The syringe stopper of claim 1 wherein said raised ribs comprises four raised ribs.

10. The syringe stopper of claim 1 wherein said base diameter is within the range of thirty percent to eighty percent of the outside diameter of said stopper body.

11. The syringe stopper of claim 1 wherein said base diameter is within the range of forty percent to sixty percent of the outside diameter of said stopper body.

12. The syringe stopper of claim 1 further including an annular rib at said distal end and an annular rib at said proximal end of said stopper body, said stopper body having an annular recess between said ribs, said recess having a diameter of less than the diameter of said ribs, said rib on said distal end further including at least one groove for allowing fluid communication therethrough.

13. The syringe stopper of claim 12 wherein said at least one groove is a plurality of grooves.

14. The syringe stopper of claim 12 wherein said groove is positioned angularly with respect to the longitudinal axis of said stopper body.

15. The syringe stopper of claim 14 wherein said at least one groove is oriented at an angle within the range of about 30° to 80° with respect to said longitudinal axis.

16. The syringe stopper of claim 1 further including means for engaging a rigid plunger rod on said proximal end of said stopper body.

17. The syringe stopper of claim 16 wherein said means for engaging includes a threaded recess in said proximal end of said stopper body.

18. The syringe stopper of claim 16 wherein said means for engaging includes a cavity in the proximal end of said stopper body having a neck or reduced diameter portion at said proximal end of said stopper body.

19. The syringe stopper of claim 16 further including a rigid elongate plunger rod having a distal end and a proximal end, said distal end of said plunger rod being connected to said proximal end of said stopper body.

20. The syringe stopper of claim 1 wherein said resilient material is selected from the group consisting of natural rubber, synthetic rubber, thermoplastic elastomers, and combinations thereof.

21. The syringe stopper of claim 1 wherein said stopper body includes at least a first annular rib at the distal end and a second annular rib at the proximal end, with said second annular rib being spaced apart from the first annular rib to form a recess located therebetween to provide a stable fluid-tight seal between the stopper body and the syringe barrel.

* * * * *